(12) United States Patent  (10) Patent No.: US 7,452,848 B2
Meier et al.  (45) Date of Patent: Nov. 18, 2008

(54) AMINE-BASED GAS HYDRATE INHIBITORS

(75) Inventors: Ingrid Kristine Meier, Asbury, NJ (US); Richard Joseph Goddard, Fogelsville, PA (US); Michael Edward Ford, Trexlertown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 639 days.

(21) Appl. No.: 11/114,274

(22) Filed: Apr. 26, 2005

(65) Prior Publication Data

US 2006/0237691 A1  Oct. 26, 2006

(51) Int. Cl.
C09K 8/52 (2006.01)
C09K 15/20 (2006.01)
(52) U.S. Cl. ......................... 507/90; 252/397
(58) Field of Classification Search ................. 252/397; 507/90
See application file for complete search history.

(56) References Cited

U.S. PATENT DOCUMENTS

| 5,741,758 | A | 4/1998 | Pakulski et al. |
| 5,841,010 | A | 11/1998 | Rabeony et al. |
| 5,879,561 | A | 3/1999 | Klomp et al. |
| 6,102,986 | A | 8/2000 | Klug et al. |
| 6,152,993 | A | 11/2000 | Klomp |
| 6,214,091 | B1 | 4/2001 | Klomp |
| 6,251,836 | B1 | 6/2001 | Duncum et al. |
| 6,281,274 | B1 | 8/2001 | Bakeev et al. |
| 6,319,971 | B1 | 11/2001 | Kelland et al. |
| 6,331,508 | B1 | 12/2001 | Pakulski |
| 6,436,877 | B1 | 8/2002 | Duncum et al. |
| 2004/0163306 | A1 | 8/2004 | Dahlmann et al. |
| 2005/0085396 | A1 | 4/2005 | Panchalingam et al. |

FOREIGN PATENT DOCUMENTS

| EP | 1676831 A1 | 7/2006 |
| WO | 94/24413 | 10/1994 |
| WO | WO 98/22557 | 11/1996 |
| WO | 98/40446 | 9/1998 |
| WO | 00/78706 A1 | 12/2000 |
| WO | WO 00/78706 A1 | 12/2000 |
| WO | 01/09082 A1 | 2/2001 |
| WO | 03/008757 A1 | 1/2003 |
| WO | 2004/111161 A1 | 12/2004 |

OTHER PUBLICATIONS

Cohen et al. ("Polycations. 4. Synthesis and Antihydrophobic Effect of Polycationic Strings", Tetrahedron Letters, 1998, 39, 8617-8620).*
Wishart et al. ("Effects of functional group substitution on electron spectra and solvation dynamics in a family of ionic liquids", Radiation Physics and Chemistry, 2005, 72, 99-104).*
European Search Report No. 06008329-2, dated Aug. 3, 2006.
* cited by examiner

*Primary Examiner*—Mark Eashoo
*Assistant Examiner*—Peter F Godenschwager
(74) *Attorney, Agent, or Firm*—Michael Leach

(57) ABSTRACT

Certain substituted amines, alkylenediamines or polyamines, and derivatives of these, are suitable for use in preventing, inhibiting, or otherwise modifying crystalline gas hydrate formation. These inhibitors include compounds from any of the following groups.

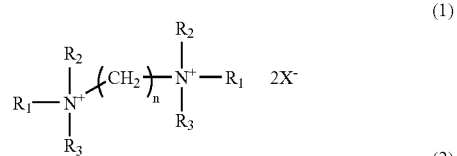

(1)

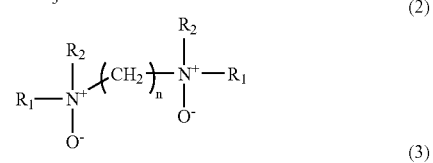

(2)

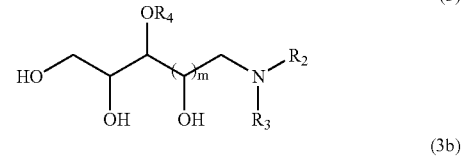

(3)

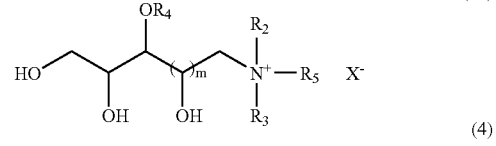

(3b)

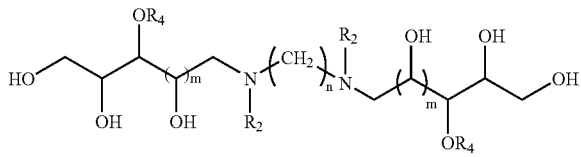

(4)

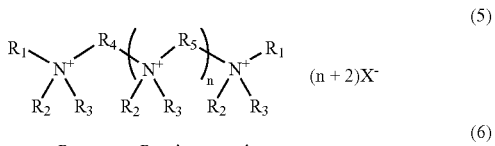

(5)

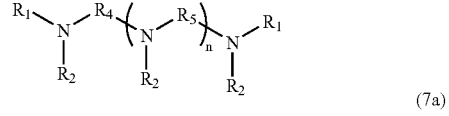

(6)

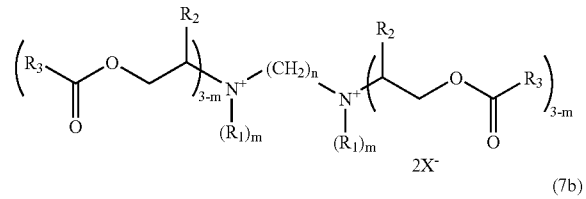

(7a)

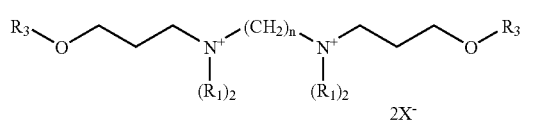

(7b)

The substituents $R_1$-$R_5$ may be hydrocarbyl groups or, in some cases, polyhydroxyalkyl groups or $(CH_2)_p$—$COO^-$ in which p is either 1 or 2.

4 Claims, No Drawings

AMINE-BASED GAS HYDRATE INHIBITORS

BACKGROUND OF THE INVENTION

Lower hydrocarbons such as methane, ethane, propane, n-butane, and isobutane are often found in crude petroleum, and are also present in natural gas streams. Water is also among the components typically present in petroleum-bearing formations. Under conditions of elevated pressure and reduced temperature, mixtures of water and many lower hydrocarbons tend to form hydrocarbon hydrates known as clathrates. Such hydrates are crystalline structures in which water has formed a cage structure around a guest molecule such as the lower hydrocarbon. For example, at a pressure of about 1 MPa, ethane can form gas hydrates with water at temperatures below 4° C.; at a pressure of 3 MPa, it can form gas hydrates with water at temperatures below 14° C. Temperatures and pressures such as these are commonly encountered for many environments in which natural gas and crude petroleum are produced and transported.

Gas hydrates are of particular interest owing to the pipeline blockages that can be produced during the production and transport of natural gas or crude petroleum. As gas hydrates form and grow inside a pipe or conduit, they can block or damage the pipeline and associated valves and other equipment. Prevention or inhibition of gas hydrate formation and agglomeration is thus sought in order to minimize unscheduled shutdowns, maintenance and repair, and to provide safer operation of production and/or transport facilities.

SUMMARY OF THE INVENTION

In one aspect, the invention provides a composition including water, a crude natural gas stream or crude petroleum stream including one or more lower hydrocarbons, and at least one compound capable of modifying gas hydrate formation. The compound is selected from the group consisting of:

a) compounds according to formula (1)

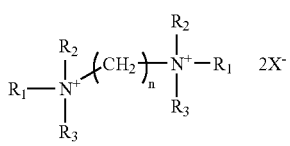

(1)

wherein $R_1$ is selected from the group consisting of $C_4$-$C_{18}$ branched alkyl, linear alkyl, alkenyl, cycloalkyl, aryl, alkaryl, and aralkyl; $R_2$ is selected from the group consisting of $C_1$-$C_8$ alkyl, alkenyl, cycloalkyl, aryl, alkaryl, aralkyl and moieties of formula (A)

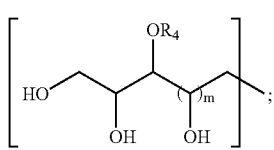

(A)

$R_3$ is $C_1$-$C_8$ alkyl, alkenyl, cycloalkyl, aryl, alkaryl, or $(CH_2)_p$—$COO^-$ wherein p is either 1 or 2; n is an integer from 2 to 14; m is an integer from 0 to 2; $R_4$ is H, α-D-glucopyranosyl, β-D-pyranosyl, or β-D-galactopyranosyl; and $X^-$ is $Cl^-$, $Br^-$, $I^-$, $OH^-$, $CH_3COO^-$, ½ $SO_4^{-2}$, or ⅓ $PO_4^{-3}$, provided that the number of $X^-$ moieties in formula (1) is reduced by one for each $R_3$ that is $(CH_2)_p$—$COO^-$;

b) compounds according to formula (2)

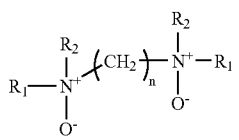

(2)

wherein $R_1$, $R_2$, and n are as defined above in relation to formula (1);

c) compounds according to formula (3)

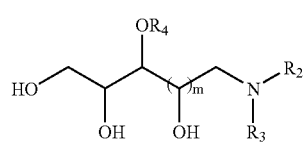

(3)

wherein m and $R_4$ are as defined in relation to formula (1), $R_2$ and $R_3$ are each independently selected from the group consisting of $C_1$ to $C_{16}$ alkyl, alkenyl, aryl, or alkylaryl groups, ethyl or propyl groups bearing a $C_1$ to $C_{16}$ alkoxy substituent, and $C_5$ or $C_6$ cycloalkyl groups, and wherein $R_3$ may also be H or have a structure according to formula (B)

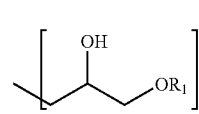

(B)

in which $R_1$ is a $C_3$ to $C_{12}$ alkyl, alkenyl, aryl, or alkylaryl group;

d) compounds according to formula (3b)

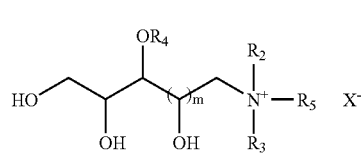

(3b)

wherein m and $R_2$-$R_4$ are as defined in relation to formula (3) and $R_3$ may also be $(CH_2)_p$—$COO^-$ wherein p is either 1 or 2; wherein $R_5$ is a $C_1$-$C_8$ alkyl, alkenyl, cycloalkyl, aryl, or alkylaryl group; and wherein $X^-$ is $Cl^-$, $Br^-$, $I^-$, $OH^-$, $CH_3COO^-$, ½ $SO_4^{-2}$ or ⅓ $PO_4^{-3}$, provided that the number of $X^-$ moieties in formula (3b) is reduced by one for each $R_3$ that is $(CH_2)_p$—$COO^-$;

e) compounds according to formula (4)

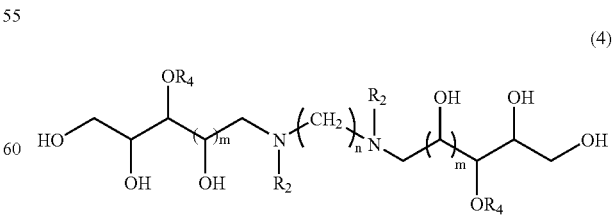

(4)

wherein m and $R_4$ are defined as in formula (A) above, each $R_2$ is independently defined as in formula (3) above and may also be of formula (B) above, and n is an integer from 2 to 14;

f) compounds according to formula (5)

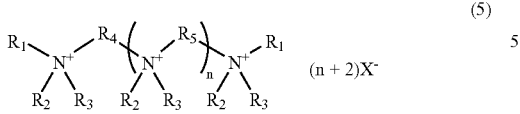

wherein $R_1$ is $C_3$-$C_{12}$ branched alkyl, linear alkyl, alkenyl, cycloalkyl, or aryl-substituted branched or linear alkyl; $R_2$ and $R_3$ are each individually selected from the group consisting of $C_1$-$C_4$ alkyl, benzyl, $C_3$-$C_5$ alkenyl, and $(CH_2)_p$—$COO^-$ wherein p is either 1 or 2, provided that not both of $R_2$ and $R_3$ are $(CH_2)_p$—$COO^-$; $R_4$ and $R_5$ are chosen independently from $C_2$-$C_6$ alkylene; n is an integer from 0 to 4; and $X^-$ is $Cl^-$, $Br^-$, $I^-$, $OH^-$, $CH_3COO^-$, $½ SO_4^{-2}$, or $⅓ PO_4^{-3}$, provided that the number of $X^-$ moieties in formula (5) is reduced by one for each $R_2$ or $R_3$ that is $(CH_2)_p$—$COO^-$;

g) compounds according to formula (6)

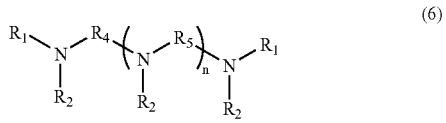

wherein $R_1$, $R_2$, $R_4$, and $R_5$ are as defined above for formula (5) except that $R_2$ cannot be $(CH_2)_p$—$COO^-$;

h) compounds according to formula (7a)

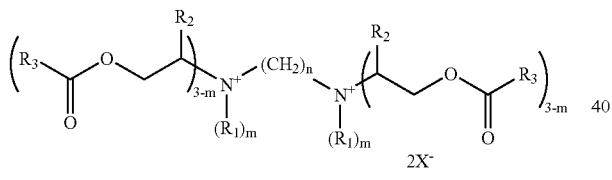

wherein each $R_1$ is independently $C_1$-$C_{20}$ alkyl or benzyl; $R_2$ is hydrogen or methyl; $R_3$ is $C_1$-$C_{18}$ alkyl; m is 1 or 2; n is an integer from 2 to 10; and $X^-$ is $Cl^-$, $Br^-$, $I^-$, $OH^-$, $CH_3COO^-$, $½ SO_4^{-2}$, or $⅓ PO_4^{-3}$; and i) compounds according to formula (7b)

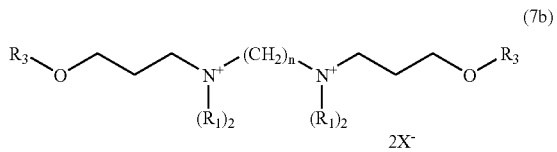

wherein $R_1$, $R_3$, n, and X are as defined above for formula (7a).

In another aspect, the invention provides a method of modifying gas hydrate formation. The method comprising contacting a crude natural gas stream or crude petroleum stream containing water and one or more lower hydrocarbons with at least one compound capable of modifying gas hydrate formation selected from groups a) through i) as defined above.

In yet another aspect, the invention provides a compound according to formula (7b) as shown above.

DETAILED DESCRIPTION OF THE INVENTION

This invention provides certain substituted amines, alkylenediamines or polyamines, and derivatives of these, suitable for use in preventing, inhibiting, or otherwise modifying crystalline gas hydrate formation. Such modification may for example slow, reduce, or eliminate nucleation, growth, and/or agglomeration of the gas hydrates. A number of classes of compounds are disclosed herein for this use, each of which will now be discussed in detail. As used herein, the term "gas hydrate" means a crystalline hydrate of a lower hydrocarbon. The term "lower hydrocarbon" means any of methane, ethane, propane, any isomer of butane, and any isomer of pentane.

The first class of gas hydrate inhibitors suitable for use according to the invention consists of certain derivatives of N,N'-dialkylalkylenediamines as shown below in formula (1).

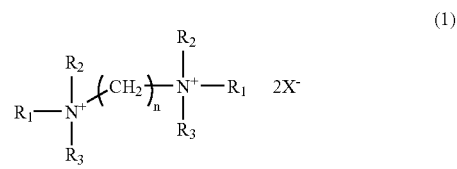

In formula (1), $R_1$ is selected from the group consisting of $C_4$-$C_{18}$ branched alkyl, linear alkyl, alkenyl, cycloalkyl, aryl, alkaryl, and aralkyl; $R_2$ is selected from the group consisting of $C_1$-$C_8$ alkyl, alkenyl, cycloalkyl, aryl, alkaryl, aralkyl and moieties of formula (A)

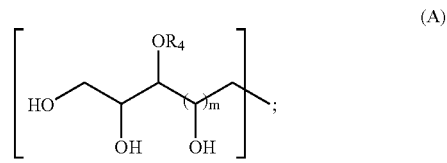

$R_3$ is $C_1$-$C_8$ alkyl, alkenyl, cycloalkyl, aryl, alkaryl, or $(CH_2)_p$—$COO^-$ in which p is either 1 or 2; n is an integer from 2 to 14; m is an integer from 0 to 2; $R_4$ is H, α-D-glucopyranosyl, β-D-pyranosyl, or β-D-galactopyranosyl; and $X^-$ is $Cl^-$, $Br^-$, $I^-$, $OH^-$, $CH_3COO^-$, $½ SO_4^{-2}$, or $⅓ PO_4^{-3}$, provided that the number of $X^-$ moieties in formula (1) is reduced by one for each $R_3$ that is $(CH_2)_p$—$COO^-$. Substituents of formula (A) above, regardless of the identity of $R_4$, will be referred to herein as "polyhydroxyalkyl" groups. It will be understood by the person of ordinary skill in the art that the use of the term "$2X^-$" in formula (1) and in formula 1(a) below is intended to indicate the amount of anion needed to provide charge neutrality.

Suitable exemplary $R_1$ groups include straight-chain or branched-chain alkyl groups such as n-butyl, 2-butyl, tert-butyl, isobutyl, n-pentyl, 2-pentyl, tert-pentyl, isopentyl, neopentyl, 2-methylpentyl, n-hexyl, isohexyl, heptyl, 2-ethylhexyl, octyl, nonyl, 3,5-dimethyloctyl, 3,7-dimethyloctyl, decyl, undecyl, dodecyl, tridecyl, tetradecyl, 3-methyl-10-ethyldodecyl, pentadecyl, hexadecyl, heptadecyl, octadecyl, cocoalkyl ($C_8H_{17}$-$C_{16}H_{33}$), and tallow ($C_{16}H_{33}$-$C_{18}H_{37}$), as well as aralkyl, aryl, alkaryl, alicyclic, bicyclic, and similar groups. Examples of such groups are cyclohexylmethyl, benzyl, pinyl, pinylmethyl, phenethyl, p-methylbenzyl, phenyl, tolyl, xylyl, naphthyl, ethylphenyl, methylnaphthyl, dimethylnaphthyl, norbornyl, and norbornylmethyl.

Suitable exemplary $R_2$ and $R_3$ groups include methyl, ethyl, n-propyl, isopropyl, n-butyl, 2-butyl, tert-butyl, isobutyl, n-pentyl, 2-pentyl, tert-pentyl, isopentyl, neopentyl, 2-methylpentyl, n-hexyl, isohexyl, heptyl, 2-ethylhexyl, octyl, cyclohexylmethyl, benzyl, phenethyl, p-methylbenzyl, phenyl, tolyl, xylyl, and ethylphenyl. Suitable exemplary $R_2$ groups also include polyhydroxyalkyl groups such as 1-deoxyglucityl, 2,3-dihydroxypropyl, and analogous 1-deoxy groups derived from mannitol, xylitol, galactitol, maltitol, and lactitol.

Compounds according to formula (1) may be prepared by any method known in the synthetic organic chemical art. For example, they may be prepared by reaction of the corresponding N,N'-di($R_1$)—N,N'-di($R_2$)alkylenediamine with an alkyl halide to introduce the group $R_3$, according to methods well known in the chemical art. In the case where $R_3$ is $(CH_2)_p$—$COO^-$, reaction with a halocarboxylic acid salt may be used, for example a salt of a haloacetic acid (see, e.g., Example 1 of U.S. Pat. No. 3,839,425; to E. I. DuPont de Nemours and Company).

If $R_2$ is a polyhydroxyalkyl group, a number of variations of $R_2$ are possible, depending upon the value of $R_4$ and m, to form a variety of compounds according to formula (1a) below.

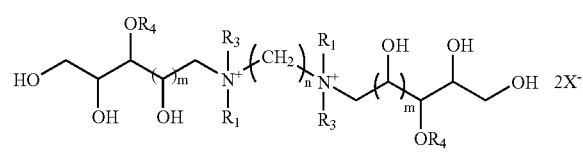

(1a)

Compounds according to formula (1a) may be obtained by any suitable procedure, for example that reported by V. I. Veksler, et. al., Zhurnal Obshchei Khimii, 50(9), 2120-2123 (1980). Although any of a variety of polyhydroxyalkyl groups may be incorporated in compounds useful in the practice of this invention, they most typically will be derived from the open-chain forms of reducing sugars, for example glucose. Exemplary polyhydroxyalkyl groups are derived from glucose; i.e., they are 1-deoxyglucityl groups. In general, polyhydroxyalkyl groups of N-(polyhydroxyalkyl)alkylamines useful for making N,N'-dialkyl-N,N'-bis(polyhydroxyalkyl) alkylenediamines of use according to the invention may be derived from any of the group of reducing sugars consisting of glucose, fructose, maltose, lactose, galactose, mannose, and xylose. Typically, the reducing sugar will be an aldose, although ketoses may also be used, and both monosaccharides and disaccharides may be used, with convenient sources of the latter including high dextrose corn syrup, high fructose corn syrup, and high maltose corn syrup. Other useful polyhydroxyalkyl groups may be derived from glyceraldehydes. In some embodiments, $R_2$ is a polyhydroxyalkyl group derived from glucose; i.e. the group is 1-deoxyglucityl. In this case, m is 2 and $R_4$ is hydrogen.

The second class of gas hydrate inhibitors useful in practicing this invention includes bis N-oxides of general formula (2)

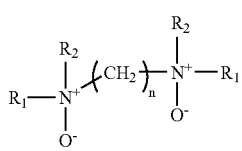

(2)

where $R_1$, $R_2$, and n are as defined above in relation to compounds of formula (1). Compounds according to formula (2) may be prepared by any method known in the synthetic organic chemical art. For example, they may be prepared by treatment of the corresponding ditertiary amine with an oxidizing agent such as hydrogen peroxide (see, e.g., U.S. Pat. No. 5,710,332, Example 4, for preparation of N-oxides of N,N-dialkylglucamines).

The case where $R_2$ is a polyhydroxyalkyl group constitutes a subclass of formula (2), shown below as formula (2a), wherein $R_1$, $R_4$, m, and n have the same meanings as defined above in relation to formula (1a).

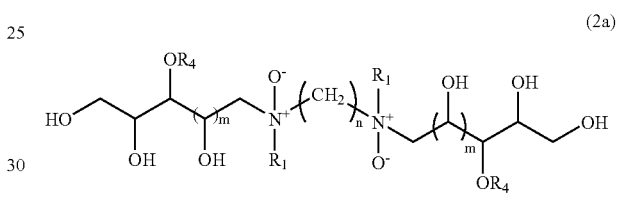

(2a)

In one embodiment, the polyhydroxyalkyl group is derived from glucose; i.e. the group is 1-deoxyglucityl. In this case, m is 2 and $R_4$ is hydrogen.

The third class of gas hydrate inhibitors useful in practicing this invention includes polyhydroxyalkyl[(di)alkyl]amines according to structure (3). If $R_3$ is H, the product is a polyhydroxyalkyl[alkyl]amine, and if $R_3$ is an alkyl or substituted alkyl group the product is a polyhydroxyalkyl[dialkyl]amine.

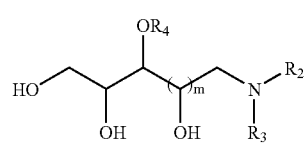

(3)

In (3), m and $R_4$ are as defined in relation to formula (1), and $R_2$ and $R_3$ are each independently selected from the group consisting of $C_1$ to $C_{16}$ alkyl, alkenyl, aryl, or alkylaryl groups, ethyl or propyl groups bearing a $C_1$ to $C_{16}$ alkoxy substituent, and $C_5$ or $C_6$ cycloalkyl groups. $R_3$ may also be H, or it may have a structure according to formula (B).

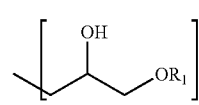

(B)

If $R_3$ is (B), the resulting compound is that shown below by (3a), in which $R_1$ is a $C_3$ to $C_{12}$ alkyl, alkenyl, aryl, or alkylaryl group.

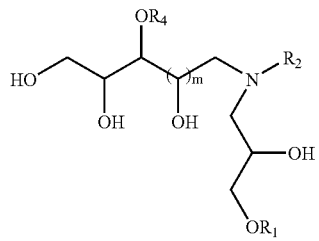
(3a)

Polyhydroxyalkyl[alkyl]amines, i.e., compounds according to formula (3) wherein $R_3$=H, may be obtained by standard reductive amination of glucose or other suitable mono- or disaccharide with the desired amine (e.g., example 1 of U.S. Pat. No. 5,625,098; to The Proctor and Gamble Company). A similar process may also be used for preparation of the polyhydroxyalkyl[dialkyl]amines (3) where $R_3$ is a hydrocarbyl group (e.g., example 3 of EP 663,389; to BASF). Polyhydroxyalkyl[dialkyl]amines of formula (3a) may be obtained by treatment of the corresponding polyhydroxyalkyl [alkyl]amines (structure (3), $R_3$=H) with a glycidyl ether of the formula shown below, for example using methods such as those described by S. Warwel, et. al., Tenside Surf. Det., 38(1), 7-14 (2001).

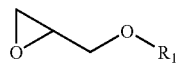

Quaternary salts of amines according to structure (3) are also included within the scope of this invention, and are represented below by structure (3b).

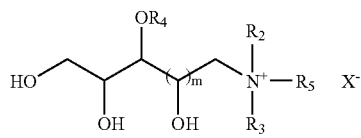
(3b)

In (3b), m and $R_2$-$R_4$ are as defined in relation to formula (3), and $R_3$ may also be $(CH_2)_p$—$COO^-$ in which p is either 1 or 2. The group $R_5$, which may be introduced by a quaternizing agent, is a $C_1$-$C_8$ alkyl, alkenyl, cycloalkyl, aryl, or alkylaryl group; and $X^-$ is $Cl^-$, $Br^-$, $I^-$, $OH^-$, $CH_3COO^-$, $½ SO_4^{-2}$, or $⅓ PO_4^{-3}$, provided that the number of $X^-$ moieties in formula (3b) is reduced by one for each $R_3$ that is $(CH_2)_p$—$COO^-$. It will be understood by the person of ordinary skill in the art that the use of the term "$X^-$" in formula (3b) is intended to indicate the amount of anion needed to provide charge neutrality.

Quaternary salts (3b) may be prepared by reaction of the corresponding dialkylamine precursor (3) with an alkyl halide (e.g., Synthetic Organic Chemistry, R. B. Wagner and H. D. Zook, John Wiley and Sons, New York, 1953, p. 668) or salt of a haloacetic acid (e.g., Example 1 of U.S. Pat. No. 3,839,425; to E. I. DuPont de Nemours and Company).

The fourth class of gas hydrate inhibitors useful in practicing this invention includes N,N'-dialkyl-N,N'-bis(polyhydroxyalkyl)alkylenediamines having the structure (4), wherein m and $R_4$ are defined as in relation to formula (1a) above, each $R_2$ is independently defined as in formula (3) above and may also be of formula (B) as described above, and n is an integer from 2 to 14. In some embodiments of the invention, each of the two $R_2$ groups in structure (4) is different. For example, one may be butyl and one may be octyl. In some embodiments, the product of structure (4) may be a statistical mixture, such as for example about 25 mole % of molecules containing two butyl groups, about 25 mole % having two octyl groups, and about 50 mole % having one of each.

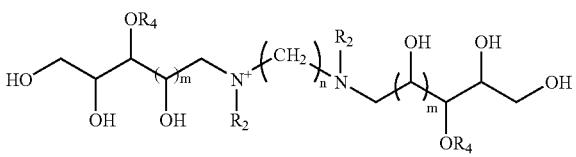
(4)

In the case where $R_2$ is according to formula (B), the compound according to structure (4) has the structure shown below as formula (4a).

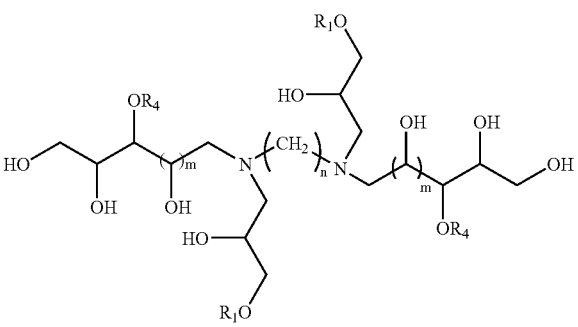
(4a)

Compounds according to formula (4a) may be prepared by reaction of compounds according to formula (4), wherein $R_2$=H, with glycidyl ethers in a manner analogous to that used for preparing polyhydroxyalkyl[dialkyl]amines (3a). Compounds (4) may be obtained by reductive alkylation of the corresponding N,N'-di(1-deoxyglucityl)-alkylenediamine with the appropriate aldehyde, for example as described on pages 4 and 5 of WO 00/076954 to SmithKline Beecham PLC, and by M. L. Fielden, et. al., Eur. J. Biochem., 268, 1269-1279 (2000). Preparation of compounds (4a) is discussed and exemplified in U.S. Patent Pub. No. 2004/0180970 A1.

The fifth class of gas hydrate inhibitors useful in practicing this invention consists of quaternary derivatives of N,N'-dialkyl polyalkylene polyamines of general formula (5).

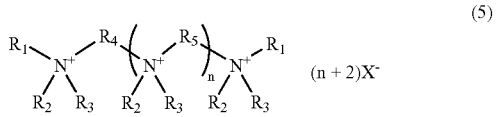
(5)

In formula (5), $R_1$ is $C_3$-$C_{12}$ branched alkyl, linear alkyl, alkenyl, cycloalkyl, or aryl-substituted branched or linear alkyl; $R_2$ and $R_3$ are each individually selected from the group consisting of $C_1$-$C_4$ alkyl, benzyl, $C_3$-$C_5$ alkenyl, and $(CH_2)_p$—$COO^-$ in which p is either 1 or 2, provided that not both of $R_2$ and $R_3$ are $(CH_2)_p$—$COO^-$; $R_4$ and $R_5$ are chosen independently from $C_2$-$C_6$ alkylene; n is an integer from 0 to 4; and $X^-$ is $Cl^-$, $Br^-$, $I^-$, $OH^-$, $CH_3COO^-$, ½ $SO_4^{-2}$, or ⅓ $PO_4^{-3}$, provided that the number of $X^-$ moieties in formula (5) is reduced by one for each $R_2$ or $R_3$ that is $(CH_2)_p$—$COO^-$. It will be understood by the person of ordinary skill in the art that the use of the term "$(n+2)X^-$" in formula (5) is intended to indicate the amount of anion needed to provide charge neutrality.

Suitable exemplary $R_1$ groups include straight-chain or branched-chain alkyl groups such as n-propyl, isopropyl, n-butyl, 2-butyl, tert-butyl, isobutyl, n-pentyl, 2-pentyl, tert-pentyl, isopentyl, neopentyl, 2-methylpentyl, n-hexyl, iso-hexyl, heptyl, 2-ethylhexyl, octyl, nonyl, 3,5-dimethyloctyl, 3,7-dimethyloctyl, decyl, undecyl, and dodecyl, as well as cyclohexylmethyl, benzyl, phenethyl, and p-methylbenzyl. Suitable exemplary $R_2$ and $R_3$ groups include methyl, ethyl, n-propyl, isopropyl, n-butyl, 2-butyl, tert-butyl, isobutyl, and benzyl. In some embodiments, $R_4$ and $R_5$ are both $(CH_2)_2$, $(CH_2)_3$, $(CH_2)_6$, or $(CH_2)_3CH(CH_3)CH_2$.

Compounds according to formula (5) may be prepared by any method known in the synthetic organic chemical art. For example, they may be prepared by alkylation under conditions known in the art of the corresponding polyamine (6), which may in turn be obtained for example according to procedures of any of U.S. Pat. Nos. 4,126,640; 4,195,152; and 6,015,852;

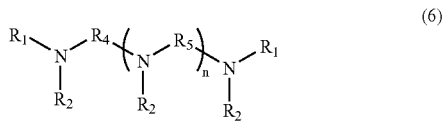

(6)

wherein $R_1$, $R_2$, $R_4$, and $R_5$ are as defined for formula (5) except that $R_2$ cannot be $(CH_2)_p$—$COO^-$. Such alkylation may for example be performed via reaction with an alkyl halide (see, e.g., Synthetic Organic Chemistry, R. B. Wagner and H. D. Zook, John Wiley and Sons, New York, 1953, p. 668). Compounds according to formula (6) themselves constitute a sixth class of gas hydrate inhibitors suitable for use according to the invention. In some embodiments, $R_4$ and $R_5$ are both $(CH_2)_2$, $(CH_2)_3$, $(CH_2)_6$, or $(CH_2)_3CH(CH_3)CH_2$.

A final class of gas hydrate inhibitors suitable for use according to the invention consists of bis quat derivatives of alkylenediamines, as shown below in formulas (7a) and (7b). Here, each $R_1$ is independently $C_1$-$C_{20}$ alkyl or benzyl; $R_2$ is hydrogen or methyl; $R_3$ is $C_1$-$C_{18}$ alkyl; m is 1 or 2; n is an integer from 2 to 10; and $X^-$ is $Cl^-$, $Br^-I^-$, $OH^-$, $CH_3COO^-$, ½ $SO_4^{-2}$, or ⅓ $PO_4^{-3}$.

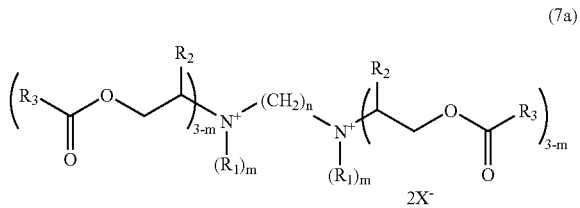

(7a)

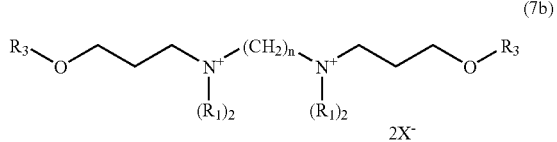

(7b)

It will be understood by the person of ordinary skill in the art that the use of the term "$2X-$" in formulas (7a) and (7b) is intended to indicate the amount of anion needed to provide charge neutrality. Examples of compounds (7a) have been described in Japanese patent JP9111660 to Lion Corp., published Apr. 28, 1997, and by T. Tatsumi, W. Zhang, T. Kida, Y. Nakatsuji, D. Ono, T. Takeda, and I. Ikeda in Journal of Surfactants and Detergents, 4, (3), 279-285 (2001). The compounds may be prepared, for example, by reaction of the corresponding tertiary amine with an α, ω-alkylene dihalide, under conditions known to those skilled in the art. The inventors believe that compounds (7b) are new compositions of matter. These may be prepared in an analogous manner to (7a), i.e., by reaction of the corresponding tertiary amine (which may for example be prepared according to the procedures disclosed in Japanese patent 2002201165, Jul. 16, 2002 to Kao Corp.) with an α, ω-alkylene dihalide.

Suitable exemplary $R_1$ groups include straight-chain alkyl groups such as methyl, ethyl, n-propyl, and n-butyl, 2-ethylhexyl, and benzyl. Suitable $R_3$ groups include straight-chain alkyl, or branched-chain alkyl, or mixed alkyl groups such as methyl, ethyl, propyl, isopropyl, n-butyl, isobutyl, n-pentyl, isopentyl, n-hexyl, cyclohexyl, n-heptyl, 2-ethylhexyl, n-octyl, isooctyl, n-nonyl, n-decyl, isodecyl, dodecyl, isododecyl, isotridecyl, tetradecyl, mixed octyl/decyl, mixed dodecyl/tetradecyl, mixed tetradecyl/dodecyl, mixed dodecyl/pentadecyl, and mixed octadecyl/hexadecyl, and mixed alkyl groups derived from natural sources such as cocoalkyl, oleyl, tallow, and stearyl. Suitable values for n include 2, 3, 4, and 6.

Use of Gas Hydrate Inhibitors

The inhibitors useful in practicing this invention can provide protection against gas hydrate formation either on their own, or in any desired mixture with one another or with other inhibitors known in the art, or with solvents or other additives included for purposes other than gas hydrate inhibition. Desired mixtures can be obtained by admixing before introduction to potential hydrate-forming fluids, or by simultaneous or sequential introduction to potential hydrate-forming fluids. Nonlimiting examples of other inhibitors that may be used in combination with inhibitors of the invention include thermodynamic inhibitors (including, but not limited to, methanol, ethanol, n-propanol, isopropanol, ethylene glycol, propylene glycol), kinetic inhibitors (including, but not limited to homopolymers or copolymers of vinylpyrrolidone, vinylcaprolactam, vinylpyridine, vinylformamide, N-vinyl-N-methylacetamide, acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-isopropylmethacrylamide, N-dodecylmethacrylamide, 1-vinylimidazole, and 1-vinyl-2-methylvinylimidazole) and agglomeration inhibitors (including, but not limited to, tetralkylammonium salts, tetraalkylphosphonium salts, trialkyl acyloxyalkyl ammonium salts, dialkyl diacyloxyalkyl ammonium salts, alkoxylated diamines, trialkyl alkyloxyalkyl ammonium salts, and trialkyl alkylpolyalkoxyalkyl ammonium salts).

Suitable exemplary solvents for making formulations containing the gas hydrate inhibitors include the aforementioned thermodynamic inhibitors as well as water, $C_4$-$C_6$ alcohols, $C_4$-$C_6$ glycols, $C_4$-$C_{10}$ ethers, $C_1$-$C_6$ mono-alkyl ethers of $C_2$-$C_6$ glycols, $C_3$-$C_{10}$ esters, and $C_3$-$C_{10}$ ketones. Other additives that may be admixed with the inhibitors of the invention include, but are not limited to, corrosion inhibitors, wax inhibitors, scale inhibitors, asphaltene inhibitors, demulsifiers, defoamers, and biocides. The amount of gas hydrate inhibitors of the invention in such a mixture can be varied over a range of 1 to 100 wt %, preferably 5 to 50 wt %.

It will be appreciated that it is very difficult, if not impossible, to predict a priori the dosages or proportions of components that will be effective in inhibiting gas hydrates in a given application. There are a number of complex, interrelated factors that must be taken into account, including, but not limited to, the salinity of the water, the composition of the hydrocarbon stream, the relative amounts of water and hydrocarbon, and the temperature and pressure. For these reasons, dosages and proportions of components are generally optimized through laboratory and field testing for a given application, using techniques well known to those of ordinary skill in the art. Two exemplary, non-limiting gas hydrate inhibitor formulations using the inventive inhibitors are as follows:

Typical Gas Hydrate Inhibitor Formulation A
10-30 wt % Inhibitor of the invention
70-90 wt % Methanol
Typical Gas Hydrate Inhibitor Formulation B
10-30 wt % Inhibitor of the invention
10-30 wt % Polymeric kinetic inhibitor
20-40 wt % Water
20-40 wt % 2-Butoxyethanol The presence of a gas hydrate inhibitor such as described above may result in a reduced rate and/or a reduced amount of hydrate formation. It may also, or instead, result in a reduction of hydrate crystal size relative to what would be seen in a given environment in the absence of the inhibitor. When added to a combined stream or static mass of water and lower hydrocarbon(s) capable of forming gas hydrates, the compounds described herein may also reduce the tendency of the gas hydrates to agglomerate. This may be of benefit during production and/or transport of these hydrocarbons. Methods for such addition are well known in the art, and are disclosed for example in U.S. Pat. No. 6,331,508 to Pakulski.

The gas hydrate inhibitors are added to a composition comprising water and one or more lower hydrocarbons in an amount that is effective to reduce or modify gas hydrate formation. Typically, such hydrate formation occurs at elevated pressures, generally at least 0.2 MPa, more typically at least 0.5MPa, and most typically at least 1.0 MPa. The inhibitor may be added to a composition containing a lower hydrocarbon before water is added, or vice versa, or it may be added to a composition already containing both. The addition may be performed before the composition is subjected to elevated pressures or to reduced temperatures, or after.

Compositions that can be treated in accordance with the present invention include fluids comprising water and guest molecules, in which the water and guest molecules together can form clathrate hydrates. The fluid mixtures may comprise any or all of a gaseous water or organic phase, an aqueous liquid phase, and an organic liquid phase, in any proportion. Typical fluids to be treated include crude petroleum or crude natural gas streams, for example those issuing from an oil or gas well, particularly an undersea oil or gas well where the temperatures may be very low and conducive to gas hydrate formation.

The gas hydrate inhibitors of the present invention may be added to the fluid mixture in a variety of ways, the lone requirement being that the additive be sufficiently incorporated into the fluid mixture to control the hydrate formation. For example, the hydrate inhibitor or additive may be mixed into the fluid system, such as into a flowing fluid stream. Thus, the inhibitor may be injected into a downhole location in a producing well to control hydrate formation in fluids being produced through the well. Likewise, the additive may be injected into the produced fluid stream at a wellhead location, or even into piping extending through a riser, through which produced fluids are transported in offshore producing operations from the ocean floor to the offshore producing facility located at or above the surface of the water. Additionally, the additive may be injected into a fluid mixture prior to transporting the mixture, for example via a subsea pipeline from an offshore producing location to an onshore gathering and/or processing facility.

Incorporating or mixing the inhibitor into the fluid mixture may be aided by mechanical means such as are well known in the art, including for example the use of a static in-line mixer in a pipeline. In most pipeline transportation applications, however, sufficient mixture and contacting will occur due to the turbulent nature of the fluid flow, and mechanical mixing aids are not necessary.

The amount of additive required to effectively inhibit hydrate formation in any particular fluid mixture will depend upon the composition of that system and the conditions of temperature and pressure to which the fluid mixture will be subjected. Generally, however, the hydrate inhibitor will be added to the fluid mixture so as to be present in an amount of from about 0.01 to about 5% by weight, and more typically from about 0.1 to about 1% by weight of the water present in the fluid mixture.

The performance properties of the instant inhibitors may be optimized for a specific application by appropriate modification of the structure of the inhibitor and the choice of the substituents $R_1$, $R_2$, $R_3$, $R_4$, and $R_5$, the number of repeating units m or n in the linking groups, and the length of the alkylene groups between the nitrogen atoms. Such optimization is routine, and within the ability of the person of ordinary skill in the art in the particular application area. Thus manipulation of these variables yields compounds that may find utility as gas hydrate inhibitors in a variety of applications, including for example those outlined in the foregoing disclosure.

In addition to their activity as gas hydrate inhibitors, compounds (1a), (2a), (3), (3a), (3b), (4), and (4a) of the present invention may exhibit increased biodegradation and lower aquatic toxicity relative to inhibitors of the prior art. More generally, inhibitors (1), (5), (6), (7a), and (7b) of the present invention, being diamine or polyamine compounds, may exhibit lower aquatic toxicity relative to some existing inhibitors.

The invention is further illustrated by the following examples, which are presented for purposes of demonstrating, but not limiting, the methods and compositions of this invention.

EXAMPLES

Examples 1-36 describe the preparation of compounds suitable for inhibiting gas hydrate formation according to the invention. Examples 37 and 38 describe experiments showing inhibition of gas hydrate formation by use of such compounds.

Example 1 illustrates preparation of N,N'-dimethyl-N,N'-dilaurylethylenediamine, an example of an intermediate in the synthesis of gas hydrate inhibitors of formula (1). (It is also an example of an inhibitor according to formula (6) in which n=0.) Examples 2-10 illustrate preparation of other N,N'-di($R_1$)-N,N'-di($R_2$)alkylenediamines.

Examples 1-10

A 300 mL Autoclave Engineers stainless steel reactor was charged with 72.4 g (0.40 mole) lauronitrile, 16.8 g (0.19 mole) of N,N'-dimethylethylenediamine, 1.45 g (dry weight basis) of a 5% palladium-on-carbon catalyst, and 48 g of isopropanol. The reactor was closed, purged with nitrogen and hydrogen, and pressurized to about 600 psig with hydrogen. The mixture was heated with stirring (1000 rpm) to 125° C., pressurized with hydrogen to 1000 psig, and maintained at this temperature and pressure via regulated hydrogen feed. After 7 hr, the mixture was cooled to room temperature and the product was removed from the reactor with filtering through an internal 0.5 μm sintered metal element. Analysis of the product by GC (Gas Chromatography) and GC-MS (Gas Chromatography-Mass Spectrometry) indicated that conversion was complete, and that the product consisted of 98+% N,N'-dimethyl-N,N'-dilaurylethylenediamine and just over 1% of N,N'-dimethyl-N-laurylethylenediamine. Vacuum distillation (190-200° C./80-100 Torr) provided pure N,N'-dimethyl-N,N'-dilaurylethylenediamine. Additional N,N'-di($R_1$)—N,N'-di($R_2$)alkylenediamines may be prepared and characterized using procedures similar to those described above. Some of these diamines are shown as Examples 2-10 in Table 1.

TABLE 1

$$R_1-N\underset{\displaystyle R_2}{\overset{\displaystyle R_2}{|}}(CH_2)_n N\underset{\displaystyle}{\overset{\displaystyle |}{-}}R_1$$

| Example | $R_1$ | $R_2$ | n |
|---|---|---|---|
| 1 | $C_{12}H_{25}$ | $CH_3$ | 2 |
| 2 | $C_6H_{11}$ | $C_2H_5$ | 2 |
| 3 | $C_6H_{11}$ | $C_2H_5$ | 6 |
| 4 | $C_8H_{15}$ | $CH_3$ | 2 |
| 5 | $C_8H_{15}$ | $CH_3$ | 6 |
| 6 | $C_{10}H_{21}$ | $CH_3$ | 2 |
| 7 | $C_{12}H_{25}$ | $C_2H_5$ | 2 |
| 8 | Cocoalkyl ($C_8H_{17}$—$C_{16}H_{33}$) | $CH_3$ | 2 |
| 9 | Cocoalkyl ($C_8H_{17}$—$C_{16}H_{33}$) | $C_2H_5$ | 2 |
| 10 | Tallow ($C_{16}H_{33}$—$C_{18}H_{37}$) | $CH_3$ | 2 |

Examples 11-15 illustrate preparation of a diquaternary salt, an example of the first class of gas hydrate inhibitor, and specifically a salt derived from Example 1 of Table 1.

Examples 11-15

To a 250 mL three-necked flask equipped with a magnetic stirrer, reflux condenser, thermometer, septum and nitrogen purge, 20 g (0.0472 mole) N,N'-dimethyl-N,N'-laurylethylenediamine and 80 mL of isopropanol were added at ambient temperature. After the diamine dissolved, 12.08 g (0.0851 mole) methyl iodide was added dropwise by syringe through the septum. The mixture was heated with stirring to 50° C. and maintained at that temperature for 16 hrs. After cooling to room temperature, removal of the solvent under vacuum with a rotary evaporator yielded N,N,N',N'-tetramethyl-N,N'-dilaurylethylenediammonium diiodide, shown as Example 11 in Table 2. The identity and purity of the product was determined by NMR analysis. Additional alkylenediammonium iodides may be prepared and characterized using procedures similar to that above. Some of these are shown in Table 2, in which X=I in all cases.

TABLE 2

$$R_1-\underset{\displaystyle R_3}{\overset{\displaystyle R_2}{\underset{|}{N+}}}(CH_2)_n\underset{\displaystyle R_3}{\overset{\displaystyle R_2}{\underset{|}{N+}}}-R_1 \quad 2X^- \quad (1)$$

| Example | $R_1$ | $R_2$ | $R_3$ | n |
|---|---|---|---|---|
| 11 | $C_{12}H_{25}$ | $CH_3$ | $CH_3$ | 2 |
| 12 | $C_6H_{11}$ | $C_2H_5$ | $CH_3$ | 2 |
| 13 | $C_8H_{15}$ | $CH_3$ | $CH_3$ | 2 |
| 14 | Cocoalkyl ($C_8H_{17}$—$C_{16}H_{33}$) | $CH_3$ | $CH_3$ | 2 |
| 15 | Tallow ($C_{16}H_{33}$—$C_{18}H_{37}$) | $CH_3$ | $CH_3$ | 2 |

Examples 16-20 illustrate preparation of bis betaine salts, i.e., examples of the class (1) of gas hydrate inhibitor where $R_3$ is $(CH_2)_p$—$COO^-$, and specifically of Example 16 in Table 3.

Examples 16-20

To a 250 mL three-necked flask equipped with a magnetic stirrer, reflux condenser, thermometer and nitrogen purge were added 20 g (0.0472 mole) of N,N'-dimethyl-N,N'-dilaurylethylenediamine, 25.54 g (0.1180 mole) of sodium iodoacetate, 80 mL of isopropanol, and 8 mL of deionized water at ambient temperature. The mixture was heated with stirring to 80° C. and maintained at that temperature for 4.5 hrs. After cooling to room temperature, the solvent was removed under vacuum with a rotary evaporator. Addition of isopropanol (about 100 mL), vacuum filtration, and subsequent removal of isopropanol under vacuum with a rotary evaporator yielded pure N,N'-di(carboxymethyl)-N,N'-dimethyl-N,N'-dilaurylethylenediammonium dihydroxide inner salt, shown as Example 16 in Table 3. Additional bis betaines may be prepared and characterized using procedures similar to those described above. Some of these are shown in Table 3, in which the compounds have the following structure.

TABLE 3

$$R_1-\underset{\displaystyle R_3}{\overset{\displaystyle R_2}{\underset{|}{N+}}}(CH_2)_n\underset{\displaystyle R_3}{\overset{\displaystyle R_2}{\underset{|}{N+}}}-R_1$$

| Example | $R_1$ | $R_2$ | $R_3$ | n |
|---|---|---|---|---|
| 16 | $C_{12}H_{25}$ | $CH_3$ | $CH_2COO^-$ | 2 |
| 17 | $C_6H_{11}$ | $C_2H_5$ | $CH_2COO^-$ | 2 |
| 18 | $C_8H_{15}$ | $CH_3$ | $CH_2COO^-$ | 2 |

TABLE 3-continued $$R_1-\underset{\underset{R_3}{|}}{\overset{\overset{R_2}{|}}{N^+}}-(CH_2)_n-\underset{\underset{R_3}{|}}{\overset{\overset{R_2}{|}}{N^+}}-R_1$$

| Example | $R_1$ | $R_2$ | $R_3$ | n |
|---|---|---|---|---|
| 19 | Cocoalkyl ($C_8H_{17}$—$C_{16}H_{33}$) | $CH_3$ | $CH_2COO^-$ | 2 |
| 20 | Tallow ($C_{16}H_{33}$—$C_{18}H_{37}$) | $CH_3$ | $CH_2COO^-$ | 2 |

Examples 21-25 illustrate preparation of several bis N-oxides, examples of class (2) gas hydrate inhibitors in which none of the substituents on either nitrogen is a polyhydroxyalkyl group.

Examples 21-25

To a 100 mL three-necked flask equipped with a magnetic stirrer, reflux condenser, thermometer, septum and nitrogen purge were added 5 g (0.0118 mole) of N,N'-dimethyl-N,N'-laurylethylenediamine and 25 mL of isopropanol at ambient temperature. The mixture was heated with stirring to 60° C., after which 3.2 g (0.028 mole; 2.4 eq.) of 30 wt % aqueous hydrogen peroxide was added dropwise from a syringe. The reaction was maintained at 60° C. for 6 hrs. After cooling to room temperature, removal of the solvent under vacuum with a rotary evaporator yielded N,N'-dimethyl-N,N'-dilaurylethylenediamine-N,N'-bis(N-oxide), shown as Example 21 in Table 4. The identity and purity of the product were determined by NMR analysis. Additional analogous alkylenediamine bis(N-oxides) may be prepared and characterized using procedures similar to those described above. Some of these are shown in Table 4.

TABLE 4

(2)

$$R_1-\underset{\underset{O^-}{|}}{\overset{\overset{R_2}{|}}{N^+}}-(CH_2)_n-\underset{\underset{O^-}{|}}{\overset{\overset{R_2}{|}}{N^+}}-R_1$$

| Example | $R_1$ | $R_2$ | n |
|---|---|---|---|
| 21 | $C_{12}H_{25}$ | $CH_3$ | 2 |
| 22 | $C_6H_{11}$ | $C_2H_5$ | 2 |
| 23 | $C_8H_{15}$ | $CH_3$ | 2 |
| 24 | Cocoalkyl ($C_8H_{17}$—$C_{16}H_{33}$) | $CH_3$ | 2 |
| 25 | Tallow ($C_{16}H_{33}$—$C_{18}H_{37}$) | $CH_3$ | 2 |

Examples 26-29 illustrate preparation of several bis N-oxides in which both nitrogen atoms are substituted with polyhydroxyalkyl groups; i.e. compounds of subclass (2a).

Examples 26-29

The procedure of Example 21 is repeated with N,N'-dioctyl-N,N'-bis(1-deoxyglucityl)ethylenediamine, with use of methanol rather than isopropanol as solvent, to prepare the compounds shown in Table 5, where $R_4$=H and m and n are both 2.

TABLE 5

(2a)

$$HO-\underset{\underset{OH}{|}}{CH}-\underset{\underset{OR_4}{|}}{CH}-CH_2-(CH_2)_m-\underset{\underset{R_1}{|}}{\overset{\overset{O^-}{|}}{N^+}}-(CH_2)_n-\underset{\underset{R_1}{|}}{\overset{\overset{O^-}{|}}{N^+}}-(CH_2)_m-\underset{\underset{OR_4}{|}}{CH}-\underset{\underset{OH}{|}}{CH}-\underset{\underset{OH}{|}}{CH}-OH$$

| Example | $R_1$ |
|---|---|
| 26 | $C_8H_{17}$ |
| 27 | $C_6H_{11}$ |
| 28 | $C_4H_9$ |
| 29 | $C_{12}H_{25}$ |

Examples 30-36 illustrate the preparation of compounds (7b).

Examples 30-36

To a 250 mL three-necked flask equipped with a magnetic stirrer, reflux condenser, thermometer, septum and nitrogen purge, 21.5 g (0.1 mole) 3-(2-ethyl)hexyloxy-1-dimethylaminopropane and 80 mL of isopropanol were added at ambient temperature. After the diamine dissolved, 4.95 g (0.05 mole) 1,2-dichloroethane was added dropwise by syringe through the septum. The mixture was heated with stirring to 50° C. and maintained at that temperature for 16 hrs. After cooling to room temperature, removal of the solvent under vacuum with a rotary evaporator yielded N,N,N',N'-tetramethyl-N,N'-bis[3-(2-ethyl)hexyloxypropyl]ethylenediammonium dichloride, shown as Example 30 in Table 6 below. The identity and purity of the product was determined by NMR analysis. Additional alkylenediammonium chlorides are prepared and characterized using procedures similar to that above, and are shown as Examples 31-36 in Table 6.

TABLE 6

(7b)

$$R_3-O\diagdown\diagup\diagdown\underset{\underset{(R_1)_2}{|}}{N^+}-(CH_2)_n-\underset{\underset{(R_1)_2}{|}}{N^+}\diagdown\diagup\diagdown O-R_3$$

$2X^-$

| Example | $R_1$ | $R_3$ | n |
|---|---|---|---|
| 30 | $CH_3$ | 2-ethylhexyl | 2 |
| 31 | $CH_3$ | n-$C_8H_{17}$/n-$C_{10}H_{21}$ | 2 |
| 32 | $CH_3$ | iso-$C_{10}H_{21}$ | 2 |
| 33 | $CH_3$ | $C_{12}H_{25}$/$C_{14}H_{29}$ | 2 |
| 34 | $CH_3$ | $C_{14}H_{29}$ | 2 |
| 35 | $CH_3$ | 2-ethylhexyl | 3 |
| 36 | $CH_3$ | 2-ethylhexyl | 4 |

Example 38 illustrates the use of the compounds described herein as gas hydrate inhibitors, with Example 37 being a control sample.

Example 37

Performance Testing—Control Sample

In this example, 100 ml of salt water (3.5 wt % NaCl) is charged to a 500 cm³ stainless steel autoclave equipped with a turbine agitator. The system is pressurized to 6.5 MPa with methane, and the pressure is maintained by the gas supply.

The autoclave temperature is reduced rapidly, at a rate of approximately 5° C. per hour, to a temperature of 15° C. The temperature is then further reduced slowly in controlled fashion at a rate of 1° C. per hour. Significant hydrate formation occurs at 9° C.

Example 38

Performance Testing—Use of Inhibitors

The operation is the same as in Example 37, but 0.5 wt %, with respect to water, of a gas hydrate inhibitor such as described herein is added to the autoclave prior to pressurization with methane. The rate of nucleation, growth, and/or agglomeration of gas hydrates is lower than that observed in control Example 37.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

What is claimed is:

1. A composition comprising water, a crude natural gas stream or crude petroleum stream comprising one or more lower hydrocarbons, and at least one compound capable of modifying gas hydrate formation selected from compounds according to the following formula:

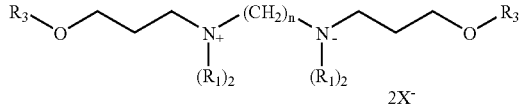

wherein each $R_1$ is independently $C_1$-$C_{20}$ alkyl or benzyl; $R_3$ is $C_1$-$C_{18}$ alkyl; n is an integer from 2 to 10; and $X^-$ is $Cl^-$, $Br^-$, $I^-$, $OH^-$, $CH_3COO^-$, ½ $SO_4^{-2}$, or ⅓ $PO_4^{-3}$.

2. The composition according to claim 1, wherein at least a portion of the water and at least a portion of the one or more lower hydrocarbons is in the form of one or more gas hydrates.

3. A method of modifying gas hydrate formation, the method comprising contacting a crude natural gas stream or crude petroleum stream comprising water and one or more lower hydrocarbons with at least one compound capable of modifying gas hydrate formation selected from compounds according to the following formula:

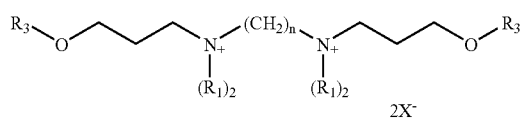

wherein each $R_1$ is independently $C_1$-$C_{20}$ alkyl or benzyl; $R_3$ is $C_1$-$C_{18}$ alkyl; n is an integer from 2 to 10; and $X^-$ is $Cl^-$, $Br^-$, $I^-$, $OH^-$, $CH_3COO^-$, ½ $SO_4^{-2}$, or ⅓ $PO_4^{-3}$.

4. A compound according to the following formula:

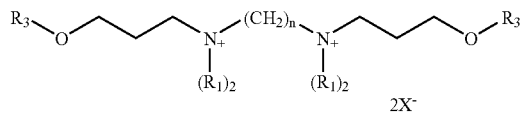

wherein each $R_1$ is independently $C_1$-$C_{20}$ alkyl or benzyl; $R_3$ is $C_1$-$C_{18}$ alkyl; n is an integer from 2 to 10; and $X^-$ is $Cl^-$, $Br^-$, $I^-$, $OH^-$, $CH_3COO^-$, ½ $SO_4^{-2}$, or ⅓ $PO_4^{-3}$.

* * * * *

UNITED STATES PATENT AND TRADEMARK OFFICE
CERTIFICATE OF CORRECTION

PATENT NO. : 7,452,848 B2 Page 1 of 1
APPLICATION NO. : 11/114274
DATED : November 18, 2008
INVENTOR(S) : Ingrid Kristine Meier, Richard Joseph Goddard and Michael Edward Ford It is certified that error appears in the above-identified patent and that said Letters Patent is hereby corrected as shown below:

Column 1, Line 31

In claim 1 delete "$N_-$" and insert --$N_+$--

Signed and Sealed this

Thirtieth Day of December, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,452,848 B2 | Page 1 of 1 |
| APPLICATION NO. | : 11/114274 | |
| DATED | : November 18, 2008 | |
| INVENTOR(S) | : Ingrid Kristine Meier, Richard Joseph Goddard and Michael Edward Ford | |

It is certified that error appears in the above-identified patent and that said Letters Patent is hereby corrected as shown below:

Column 17, Line 31

In claim 1 delete "$N_-$" and insert --$N_+$--

This certificate supersedes the Certificate of Correction issued December 30, 2008.

Signed and Sealed this

Third Day of February, 2009

JOHN DOLL
*Acting Director of the United States Patent and Trademark Office*